United States Patent
Kashyap

(10) Patent No.: US 11,010,850 B1
(45) Date of Patent: May 18, 2021

(54) METHOD AND SYSTEM FOR MOBILE HIGH-ENERGY RADIATION TREATMENT ENVIRONMENT

(71) Applicant: VARIAN MEDICAL SYSTEMS, INC., Cham (CH)

(72) Inventor: Srinath Hariharan Kashyap, Palo Alto, CA (US)

(73) Assignee: Varian Medical Systems, Inc., Cham (CH)

( * ) Notice: Subject to any disclaimer, the term of this patent is extended or adjusted under 35 U.S.C. 154(b) by 73 days.

(21) Appl. No.: 16/267,339

(22) Filed: Feb. 4, 2019

Related U.S. Application Data

(63) Continuation of application No. 14/040,602, filed on Sep. 27, 2013, now Pat. No. 10,210,588.

(51) Int. Cl.
*G06Q 50/22* (2018.01)
*G16H 40/63* (2018.01)
*G06Q 10/06* (2012.01)
*G16H 40/20* (2018.01)

(52) U.S. Cl.
CPC ......... *G06Q 50/22* (2013.01); *G06Q 10/0633* (2013.01); *G16H 40/20* (2018.01); *G16H 40/63* (2018.01)

(58) Field of Classification Search
None
See application file for complete search history.

(56) References Cited

U.S. PATENT DOCUMENTS

| | | | |
|---|---|---|---|
| 6,772,331 B1 | 8/2004 | Hind | |
| 6,961,604 B1* | 11/2005 | Vahasalo | G01R 33/283 |
| | | | 324/318 |
| 7,574,369 B1 | 8/2009 | Borza | |
| 8,152,071 B2 | 4/2012 | Doherty et al. | |
| 2003/0086526 A1 | 5/2003 | Clark | |
| 2005/0218348 A1 | 10/2005 | Fehrenbacher et al. | |
| 2009/0069640 A1 | 3/2009 | Rietzel et al. | |
| 2011/0122995 A1 | 5/2011 | Ferro, Jr. | |
| 2011/0205016 A1 | 8/2011 | Al-Azem et al. | |
| 2013/0048883 A1* | 2/2013 | Simon | A61N 5/1048 |
| | | | 250/492.3 |
| 2014/0275970 A1 | 9/2014 | Brown | |

* cited by examiner

*Primary Examiner* — Devin C Hein
(74) *Attorney, Agent, or Firm* — Foley & Lardner LLP

(57) ABSTRACT

The present invention is directed to a method, system, and article of manufacture of a treatment environment engine on a mobile device to allow performance of workflow tasks inside of a high radiation medical procedure room. The treatment environment engine comprises a capturing module, a synchronization module, and a medical device control console component for capturing data (e.g., images or text) on the mobile device inside the medical procedure room and synchronizing the data via a wireless network with a medical device control console located outside the medical procedure room.

20 Claims, 13 Drawing Sheets

102

104

METHOD AND SYSTEM FOR MOBILE HIGH-ENERGY RADIATION TREATMENT ENVIRONMENT

CROSS-REFERENCE TO RELATED APPLICATIONS

This application is a continuation of U.S. patent application Ser. No. 14/040,602, filed on Sep. 27, 2013, which is herein incorporated by reference for all purposes.

TECHNICAL FIELD

The present invention relates generally to radiation therapy and, more particularly, to workflow in the treatment of radiation therapy.

BACKGROUND

Clinical workflow in a medical procedure room using a major medical device like computerized tomography (CT) or magnetic resonance imaging (MRI), or radiation therapy linear accelerator machine tends to be cumbersome and manually driven without the benefits of the latest mobile technologies. Typical actions that are performed inside the medical procedure room include patient setup, first day patient setup position definition and recording, daily/regular Source to Skin Distance (SSD) read-out, daily/regular field size confirmation verification, pre-setup patient verification, and machine accessory verification. The completion of these workflow actions require recordation back to a computer information system, which is placed outside the medical procedure room.

In a conventional solution, the execution of the following workflows requires several more steps. First, record the data inside the medical procedure room on an intermediate device. This may be accomplished by using stand-alone recording devices inside the room, such as a camera to capture setup photos, physical taking of notes (on notepads or post-it notes) to capture setup notes/SSD, and standalone devices like a tablet or smart phone to take electronic notes. Second, a medical personnel (e.g., a physician, a nurse, or a technician) walks to a medical device control console (also referred to as "treat workstation" or "Verify and Record (V&R) console workstation") outside the device room. Third, the medical personnel enters the data into the Verify and Record console application in one of several ways. For example, the medical personnel can (a) set up a photo transfer by (i) connecting the camera to the treatment workstation via a physical cable or wireless connection, (ii) opening the setup photo import feature in the treatment workstation, (iii) selecting the correct photo from the list of photos captured on the camera's memory card, and (iv) assigning the photo to the correct field/fields in the correct radiation therapy plan of the current patient, or (b) manually enter the setup note or the SSD written down on the physical paper-pad/post-it into the correct field on the console application. In addition, the verification of patient and machine accessories can be conducted by scanning electronic identifier tags like bar codes for patient and machine accessory verification requires a dedicated tag reader like a bar code scanner installed inside the device room.

One drawback of conventional solutions is the inconvenience and manually intensive approach. The medical personnel has to walk out of the medical procedure room and perform additional actions on the device control console computer, located outside the medical procedure room, in order to complete a workflow. For example, the medical personnel attaches the camera via the connector cable to the computer, launch the photo import feature on the console application to setup photo transfer. Another drawback is the increased probability and risk of human error during the transfer, such as the user may attach the setup photo to the wrong plan/field, or the user may enter the value or notes incorrectly from the physical notepad into the system due to illegibility of the note or an error in copying. There also potentially could be an increased risk in the introduction of an error as the user has to perform the action (like entering the setup note or the SSD) twice—once inside the medical procedure room, and then again at the console outside the medical procedure room. A further drawback is the higher costs with the existing solutions, such as purchasing an additional device like a bar code scanner connected with the medical device for reading the popular QR codes.

Accordingly, it is desirable to have a mobile system and method for simplifying the workflow process in a high-energy radiation treatment environment.

SUMMARY

The present invention is directed to a method, system, and article of manufacture of Treatment Environment Application for Mobile device ("TEAM") on a mobile device to allow performance of workflow tasks inside a high radiation medical procedure room. The treatment environment engine comprises a capturing module, a synchronization module, and a medical device control console component for capturing data (e.g., images or text) on the mobile device inside the medical procedure room and synchronizing the data via a wireless network with a medical device control console located outside the medical procedure room.

In a first embodiment, the wireless networked treatment environment is implemented in a singular medical procedure room. In a second embodiment, the wireless networked treatment environment is implemented with multiple medical procedure rooms with multiple radiation therapy treatment devices. In a third embodiment, the wireless networked treatment environment is implemented with multiple medical procedure rooms, which share a common Wi-Fi network. A dual wireless router or repeater is used to set up and create a continuous wireless network specific to each installed medical device that is accessible from both inside the treatment room and outside the treatment room in the control area. This allows access to the same application from both inside and outside the device room without KVM extenders (KVM being an abbreviation for keyboard, video or visual display unit, mouse).

The wireless networked treatment environment provides the ability in acquiring and assigning setup photos from inside the treatment room. The wireless networked treatment environment further provides the capability to save notes like setup notes and analog value read-outs like SSD from inside the treatment room. Wireless access point in the medical procedure room is provided by using a wireless access point inside the medical procedure room to ensure wireless access from inside the medical procedure room. This setup ensures continuous wireless network availability even inside heavily shielded device rooms like the concrete/lead-lined rooms used for high-energy radiation therapy.

Broadly stated, a computer-implemented method for performing a workflow inside a medical procedure room comprises synchronizing a patient session loaded onto a computer console located outside a medical procedure room and a mobile device located inside the medical procedure room, the patient session being associated with a patient; capturing by the mobile device, a mobile device data generated from workflow performed on the patient inside the medical procedure room to produce a captured data; transforming the captured data into a modified data that comprises the current patient information and a treatment plan; and storing the modified data from the mobile device inside the medical procedure room by wireless transmission to the computer console located outside the medical procedure room.

The present invention advantageously reduces the amount of time per patient session. The TEAM provides a faster workflow to complete the treatment workflows relative to prior solution. This in turn results in shorter treatment sessions for the patient and the potential to treat a greater number of patients per day. Second, the present invention further eliminates extraneous objects required in the device room, e.g. a camera, a paper-pad etc. The TEAM also provides a safer and more robust workflow by synchronizing instantly the data (setup photos, notes, SSD values etc.) that are generated inside the medical procedure room with the medical device control console located outside the medical procedure room. Third, the same application is used in in-room and in the treatment area. Because the TEAM on a mobile device can be used both inside the treatment room and outside in the treatment area, the user is able to interact with the same application to perform the workflow irrespective of his location. Fourth, each mobile device is configured to the Wi-Fi network specific to a particular medical device control console. This eliminates the risk of receiving incorrect patient context from a different device. Fifth, the present invention provides a lower cost of deployment by using a mobile application deployment model, which allows newer versions of the TEAM to be deployed remotely, for example, from an online application store like the Apple® App Store™.

The structures and methods of the present invention are disclosed in the detailed description below. This summary does not purport to define the invention. The invention is defined by the claims. These and other embodiments, features, aspects, and advantages of the invention will become better understood with regard to the following description, appended claims, and accompanying drawings.

DESCRIPTION OF DRAWINGS

The invention will be described with respect to specific embodiments thereof, and reference will be made to the drawings, in which.

DETAILED DESCRIPTION

Figure 1:
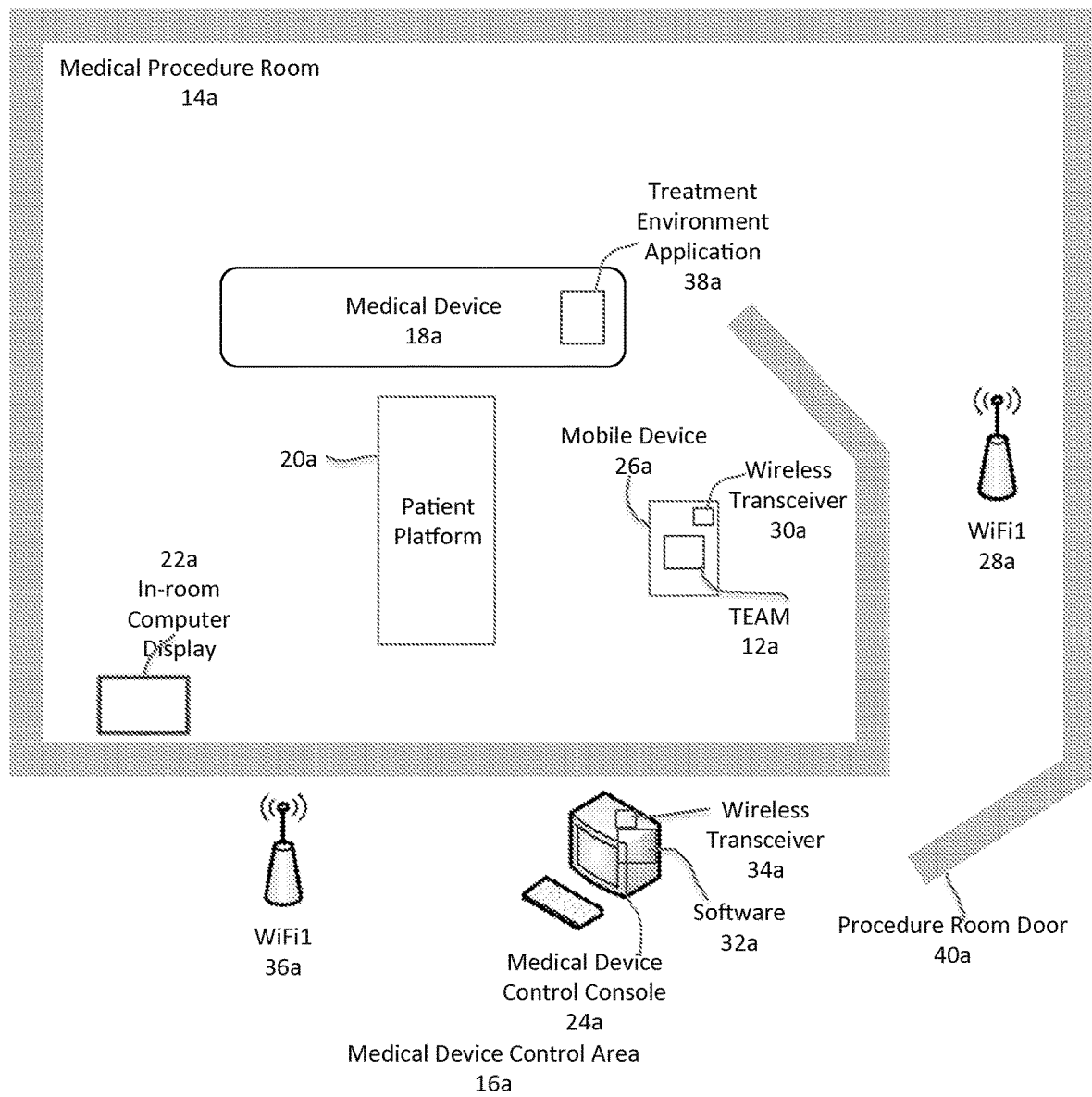
FIG. 1 is a block diagram illustrating a first embodiment of a wireless networked treatment environment in a singular medical procedure room in accordance with the present invention.

A description of structural embodiments and methods of the present invention is provided with reference to FIGS. 1-13. It is to be understood that there is no intention to limit the invention to the specifically disclosed embodiments but that the invention may be practiced using other features, elements, methods, and embodiments. Like elements in various embodiments are commonly referred to with like reference numerals.

FIG. 1 is a block diagram illustrating a first embodiment of a high-energy radiation treatment environment 10a in a single room construction with a wireless network accessed through a TEAM 12a (also referred to as "mobile treatment environment engine," "mobile treatment environment application," or "mobile operating system"). The high-energy radiation treatment environment 10a comprises a first sub-environment that is subject to high-energy radiation, hereinafter referred to as medical procedure room 14a, and a second sub-environment in a conventional room setting, hereinafter referred to as medical device control area 16a. Inside a medical procedure room 14a, as depicted in FIG. 1, a medical radiation device 18a (also referred to as a radiation therapy treatment device), such as TrueBeam from Varian Medical Systems, with a patient platform 20a are provided for treatment of a patient. A computer display 22a is also made available inside the medical procedure room 14a for one-way communication from a medical device control console 24a, which is located outside the medical procedure room 14a and within the medical device control area 16a. The medical device control console 24a is typically connected through a wired network for supplying information, unidirectional, from the medical device control console 24a to the computer display 22a inside the medical procedure room 14a. A desktop computer is generally not placed inside the medical procedure room 14a to avoid burning out the computer by the high radiation from radiation therapy treatment device 18a. Therefore, a caretaker, such as a doctor, a nurse, or a technician, will not be able to enter data about the patient while inside the medical procedure room 14a. In this embodiment, a first wireless device 28a (also referred to as Wi-Fi Receiver) is placed inside the medical procedure room 14a for wireless bidirectional communications between a mobile device 26a (also referred to as VTab) inside the medical procedure room 14a and the medical device control console 24a, in the medical device control area 16a, through a first wireless device 28a and via a second wireless device 36a that is placed outside the medical procedure room 14a and within the medical device control area 16a. In one embodiment, the mobile device 26a includes but not limited to a portable device (including a smartphone like iPhones, a mobile phone, a mobile device like iPods, a wearable mobile device like iWatch or Google Glass, a tablet computer like iPads, and a browser-based notebook computer like Chromebook) with a processor, a memory, a screen, with connection capabilities of Wireless Local Area Network (WLAN) and Wide Area Network (WAN). The mobile phone is configured with a full or partial operating system (OS) software, which provides a platform for running basic and advanced software applications. In some embodiments, the radiation therapy treatment device 18a includes an optional treatment environment application 38a for communication with the mobile device 26a or the medical device control console 24a.

Figure 2:
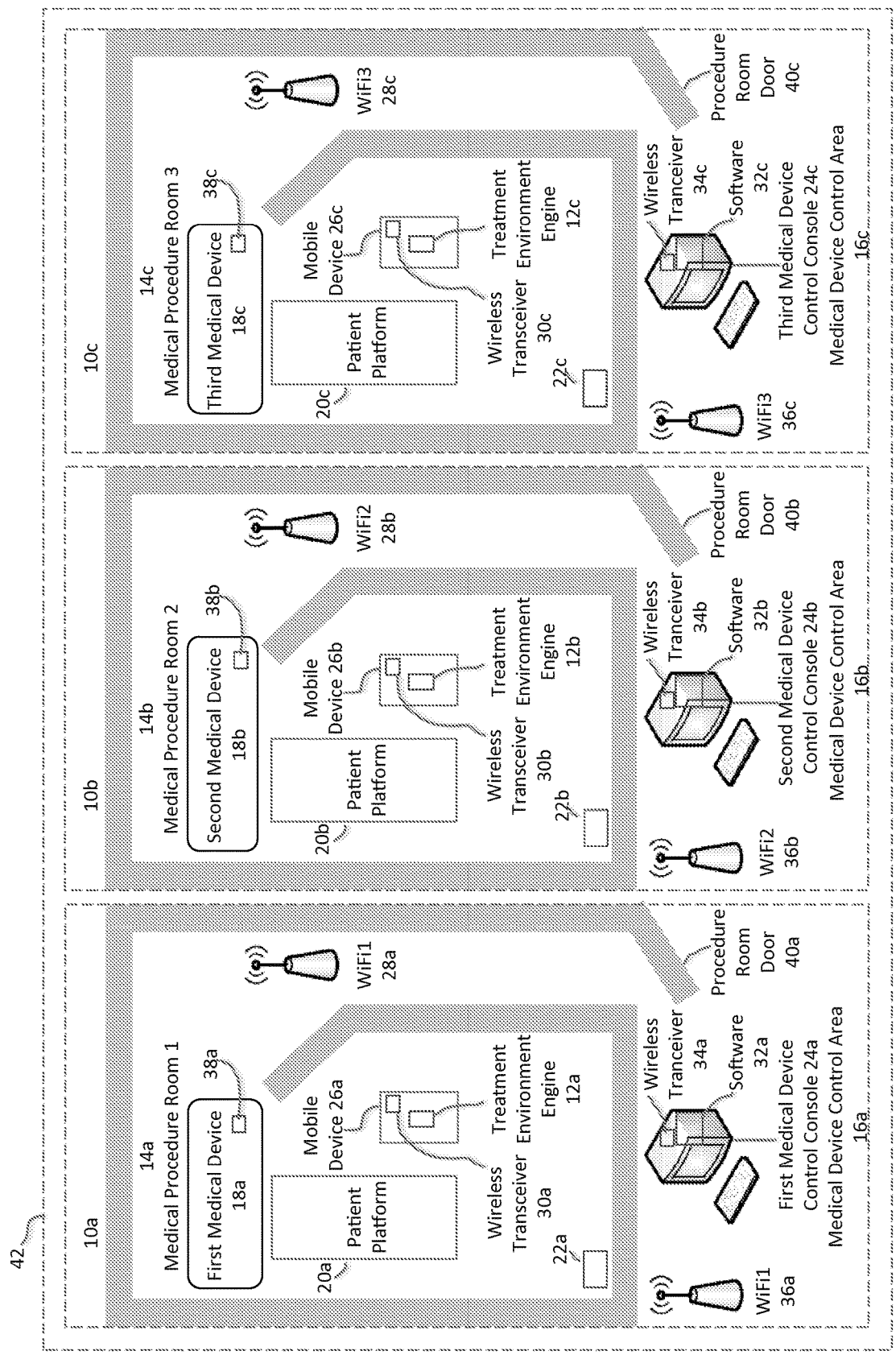
FIG. 2 is a block diagram illustrating a second embodiment of a wireless networked treatment environment with multiple medical procedure rooms in accordance with the present invention.

FIG. 2 is a block diagram illustrating a second embodiment of a high-energy radiation treatment environment 42 in multiple medical procedure rooms 10a, 10b, 10c with a wireless network accessed through respective mobile treatment environment applications 12a, 12b, 12c. When a treater observes and diagnoses a patient, who is sitting or lying on the patient platform 20a and is being scanned by the radiation therapy treatment device 18a, the treater can, in real time, enter text or image data to the mobile device 26a. The mobile treatment environment engine 12a in the mobile device 26a is configured to transmit the input data through a wireless transceiver 30a via the first wireless router/access point 28a. The medical device control console 24a includes a treatment environment application 32a, which is configured to send/receive text or image data to/from mobile device 26a to a wireless transceiver 34a, which communicates wirelessly with the wireless router/access point 36a.

A first radiation therapy treatment device 18a is set up and loaded with an optional treatment environment application 38a, which communicates with the software application 32a in the medical device control console 24a. With the addition to the mobile device 26a, the treater is now able to capture and transfer text or image data of a patient inside the medical procedure room 14a and have the text or image data transferred or synchronized with the patient session data that resides in the medical device control console 24a. The medical device control console 24a, in turn, has the capability to communicate the updated data to the optional treatment environment application 38a in the radiation therapy treatment device 18a.

The medical procedure room 14a is a high-radiation environment for diagnoses and treatment of patients. A procedure room door 40a, which opens and closes, is part of the medical procedure room 14a. When a radiation treatment is in progress, the procedure room door 40a, when it is closed, prevents the radiation from leaking into other spaces and reaching other individuals. In an alternative embodiment, a medical procedure room may not have a door but instead has a built-in labyrinth to keep radiation out without having a door.

The high-radiation treatment 42 is structured with multiple medical procedure rooms, which in this embodiment are shown as three exemplary medical procedure rooms 14a, 14b, 14c. The medical procedure rooms 14b and 14c both contain the same or similar setups as the first medical procedure room 14a. The first mobile device 26a, in the medical procedure room 14a, is able to communicate text or image data to a second mobile device 26b, or a second device control console 24b, in the second medical procedure room 14b, and is able to communicate with a third mobile device 26c, or a third device control console 24c, in the third medical procedure room 14c. In this regard, text or image data captured by the first radiation therapy treatment device 18a, in the first medical procedure room 14a, and the second medical device 18b, in the second medical procedure room 14b, and the third medical device 18c, in the third medical procedure room 14c, can all be shared directly through communication corresponding to the first medical device control console 24a, the second device control console 24b, and the third device control console 24c.

Similarly, the second high-radiation environment treatment 10b is constructed with the second medical procedure room 14b and the medical device control area 16b. The second medical procedure room 14b includes a second medical device 18b, a second patient platform 20b, the mobile device 26b, and a wireless device 28b. The second mobile device 26b includes a treatment environment engine 12b for capturing text or image data for a patient to transmit to a wireless device 28b. The second device control console 24b includes a second software 32b for sending or receiving text or image data through a wireless transceiver 34b to the wireless device 36b.

In the same fashion, the third high-radiation environment treatment 10c is constructed with the third medical procedure room 14c and the medical device control area 16c. The third medical procedure room 14c includes a third medical device 18c, a third patient platform 20c, the mobile device 26c, and a wireless device 28c. The third mobile device 26c includes a treatment environment engine 12c for capturing text or image data for a patient to transmit to a wireless device 28c. The second device control console 24c includes a third software 32c for sending or receiving text or image data through a wireless transceiver 34b to the wireless device 36c.

Figure 3:
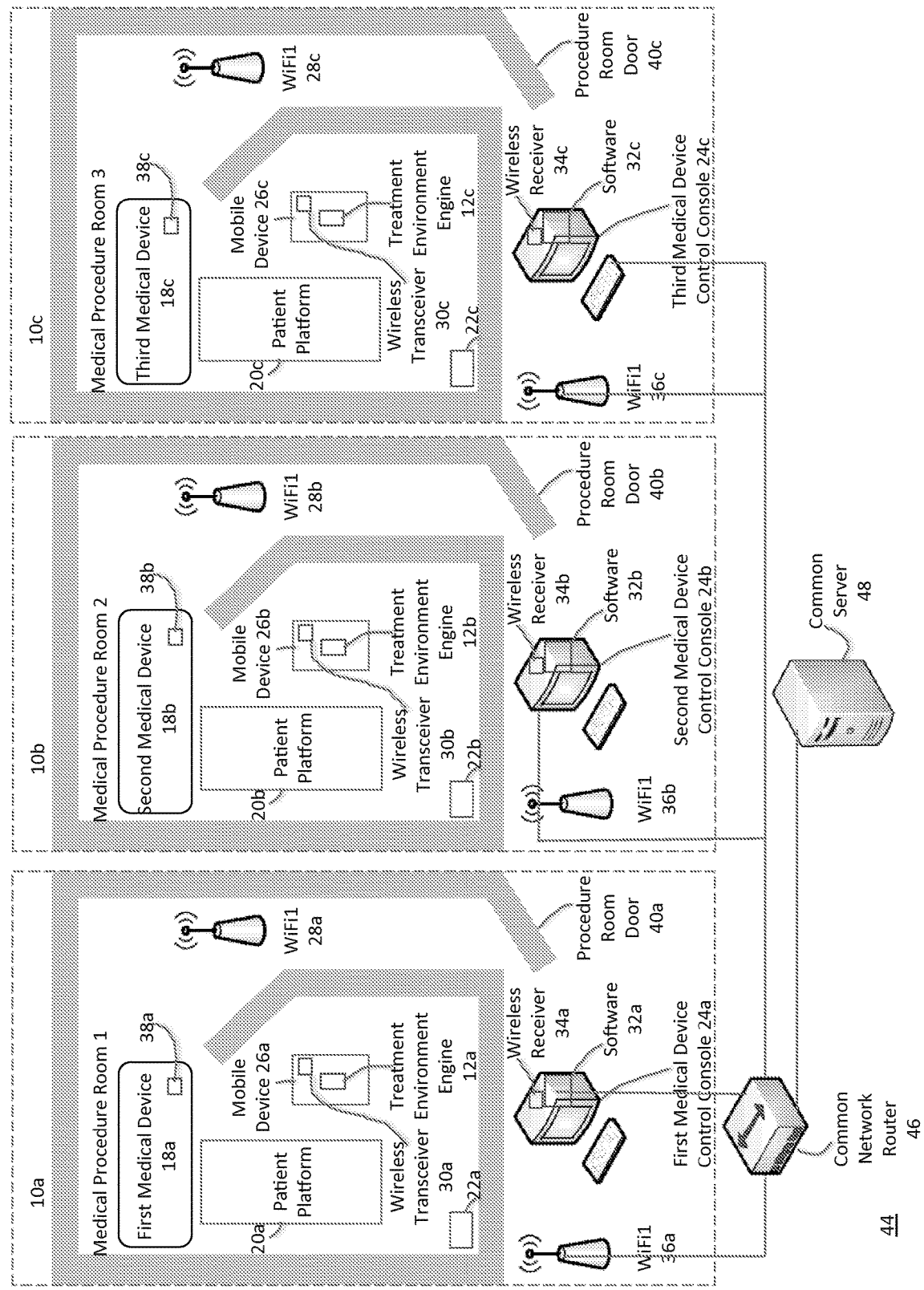
FIG. 3 is a block diagram illustrating a third embodiment of a wireless networked treatment environment with multiple medical procedure rooms that share a common Wi-Fi network in accordance with the present invention.

FIG. 3 is a block diagram illustrating a third embodiment of a wireless networked treatment environment 44 with multiple medical procedure rooms that share a common Wi-Fi network router 46. In this embodiment, the multiple medical procedure rooms are adjacent to each other, but other room configurations are feasible to practice the invention. The wireless networked treatment environment 44 has a network configuration in which the common Wi-Fi network (connected via a common router 46) is shared across multiple medical procedure rooms including the first medical procedure room 10a, the second medical procedure room 10b, and the third medical procedure room 10c. Each of the mobile devices 26a, 26b, 26c is associated with a unique identifier (e.g., the UDID for iPhone and iPads) that configures with the common server 48. The common server 48 contains a mapping between the mobile device 26a and the radiation therapy treatment device 18a, a mapping between the mobile device 26b and the medical device 18b, and a mapping between the mobile device 26c and the medical device 18c. In this embodiment, one advantage of the wireless networked treatment environment 44 is that just one wireless network can be used in the medical device control area instead of one per treatment room.

Figure 4:
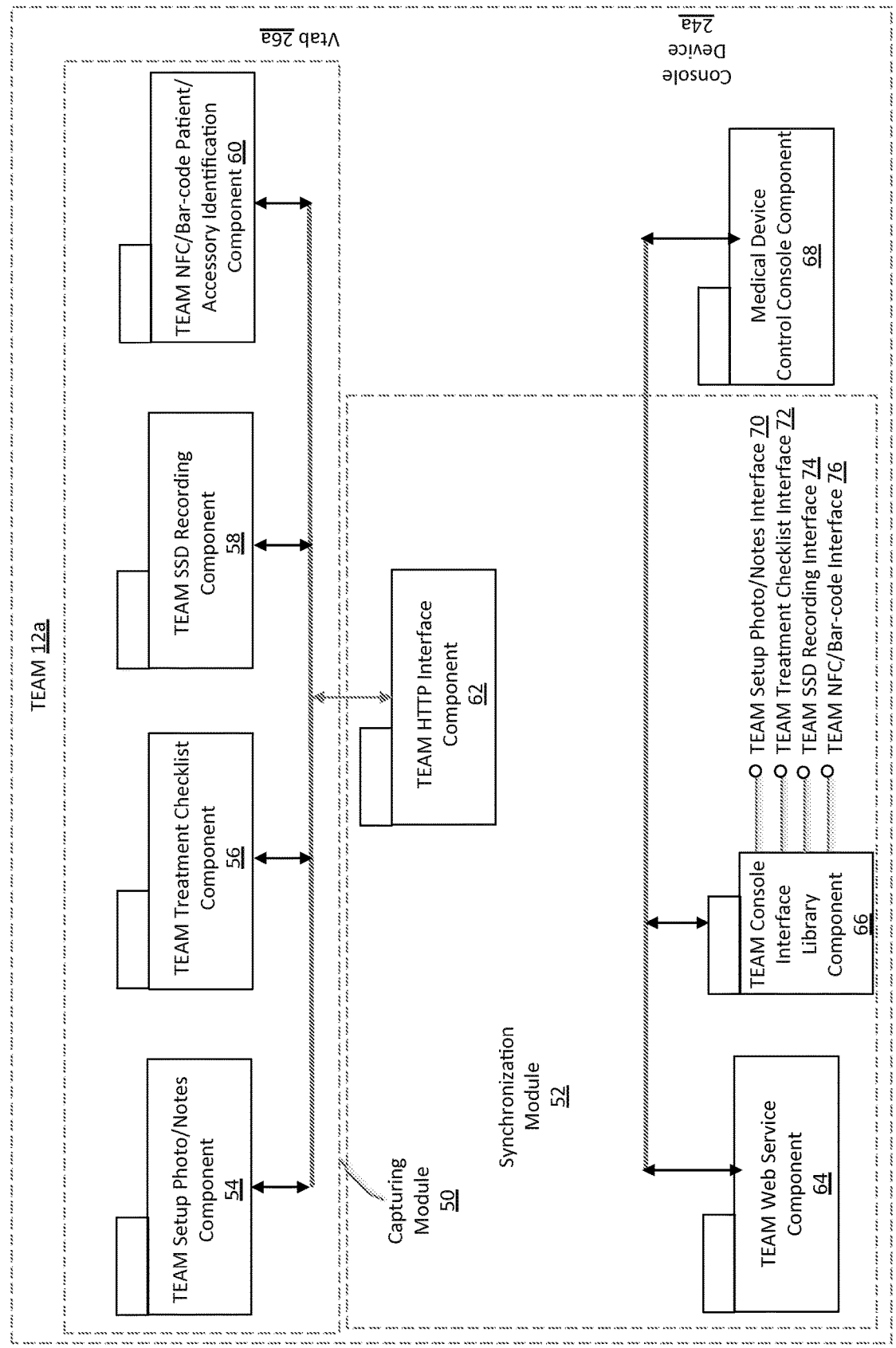
FIG. 4 is a block diagram illustrating the TEAM for use in the wireless networked treatment environments in accordance with the present invention.

FIG. 4 is a block diagram illustrating the mobile treatment engine 12a for use in the wireless networked treatment environments; there are three environments: 10a, 42, and 44. The mobile treatment engine 12a includes a capturing module 50 for capturing image or text into the mobile device 26a, a synchronization module 52 for synchronizing data between the mobile device 26a and the medical device control console 24a, and a medical device control console component 68. The operations of the capturing module 50 are associated with the mobile device 26a, while the operations of synchronization module 52 are associated with the medical device control console 24a. The capturing module 50 contains a TEAM (Treatment Environment Application for a Mobile device) setup photo/notes component 54, a TEAM treatment checklist component 56, a TEAM SSD recording component 58, and a TEAM NFC/Bar-code patient/accessory identification component 60. The synchronization module 52 contains a TEAM HTTP interface component 62, a TEAM web service component 64, and a TEAM console interface library 66. The TEAM console interface library component 66 has four interfaces for coupling to a TEAM set up photo/notes interface 70, a TEAM treatment checklist interface 72, a TEAM SSD recording interface 74, and a TEAM NCF/Bar-code interface 76. There are many types of information that the capturing module 50 in the mobile device 26a captures in which the synchronization module 52 synchronizes with the medical control console 24a outside the medical procedure room 14a that includes, but not limited to, photos, written text, update of medical history and condition, etc. The mobile treatment engine 12a comprises a user interface module, coupled to the capturing module, for providing at least one touch screen interface function including the TEAM photo/notes interface 70, the TEAM treatment checklist interface 72, the TEAM SSD recording interface 74, and the TEAM NFC/bar code interface 76.

Within the capturing module 50 each of the four components 54, 56, 58, and 60 serve different functional purposes. The TEAM setup photo/notes component 54 is configured to capture photos and written notes as inputted into the mobile device 26a. The TEAM treatment checklist component 56 is configured to generate a checklist associated with a particular patient, in which the checklist can be updated throughout the process. The TEAM SSD recording component 58 is configured to allow the user to enter the Source to Skin Distance (SSD) on the mobile device 26a. The TEAM NFC/Bar-code patient/accessory identification component 60 is configured to detect and process a bar-code identification associated with a patient by capturing the bar-code via the mobile device's camera or wireless bar code reader. Alternatively, The TEAM NFC/Bar-code patient/accessory identification component 60 is configured to detect and process a RFID tag associated with a patient through an NFC/RFID reader.

The synchronization module 52 is configured to serve as an intermediary between the mobile device 26a and the device control console 24a through the TEAM HTTP interface component 62, the TEAM web service component 64, the TEAM console interface library component 66, and the medical device control console component 68. The TEAM HTTP interface component 62 acts as one exemplary interface to the capturing module 50, but this invention is not limited to an HTTP interface and other types of interfaces are applicable to the present invention. The TEAM HTTP interface component 62 operates as a medium for information transfer between component 54, 56, 58, and 60 in the capturing module 50 with the synchronization module 52. The TEAM web service component 64 is configured to provide a multitude of web functions in the synchronization module 52. The TEAM console interface library component 66 is configured to provide different types of interfaces, including TEAM setup photo/notes interface 70, the TEAM treatment checklist interface 72, the TEAM SSD recording interface 74, and the TEAM NFC/Bar-code interface 76. The medical device control console component 68, not part of the synchronization module 52 or the capturing module 50, is configured to operate with the medical device control console 24a.

Figure 5:
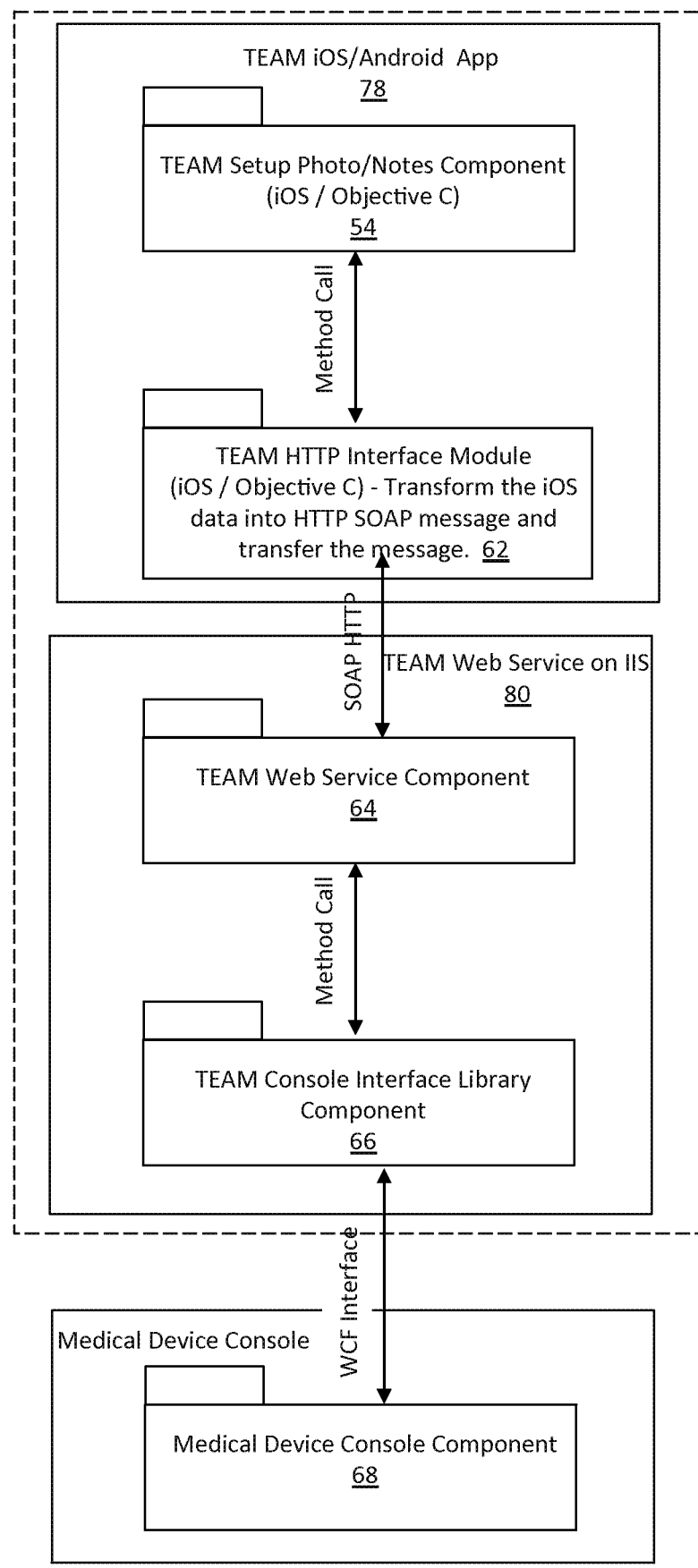
FIG. 5 is a block diagram illustrating the interactions between the mobile operating system, the web service, and the medical device control console in accordance with the present invention.

FIG. 5 is a block diagram illustrating the interactions between a mobile operating system 78, the web service, and the medical device control console 24a. The mobile operating system 78 can be selected from one of the commercially available software, such as Android, iOS, or Windows Mobile. In this illustration, the TEAM setup photo/notes (iOS/Objective C) component 54, resident on the mobile device 26a, is configured to capture photo images or written text entry by a physician, nurse, or technician in the medical procedure room 14a, and transforms the captured data (or generated data) into modified data that includes the current patient, treatment plan and field context information such as the patient ID, the plan UID, and the field ID. When the modified data is synchronized between the mobile device 26a and the medical device control console 24a, the medical device control console 24a is able to store the specific modified data associated with a particular patient given that the TEAM set photo/notes (iOS/Objective C) component 54 associates the photo images or written text captured to a particular patient session. The modified data provides advantages that a newly captured images or text by the mobile device 26a is automatically linked to that particular patient storage information, and thus avoiding mis-association or human errors during transport. The TEAM HTTP interface component (iOS/Objective C) component 62, bidirectional communicatively coupled with the TEAM setup photo/notes component 54 on a method call, is configured to transform the mobile operating system (e.g. iOS) data into HTTP SOAP (Simple Object Access Protocol) message and transfer the message.

A TEAM web service on Internet Information Services (IIS) 80 includes the TEAM web service component 64 and the TEAM console interface library component 66. The TEAM web service component 64, bidirectional communicatively coupled with TEAM HTTP interface component (iOS/Objective C) component 62 for communicating HTTP SOAP messages, is configured to provide web services through a web server. The TEAM console interface library component 66 is bidirectional communicatively coupled between the TEAM web service component 64 for a method call and the medical device control console component 68 to establish a Windows Communication Foundation (or WCF) interface to the medical device control console component 68.

Figure 6:
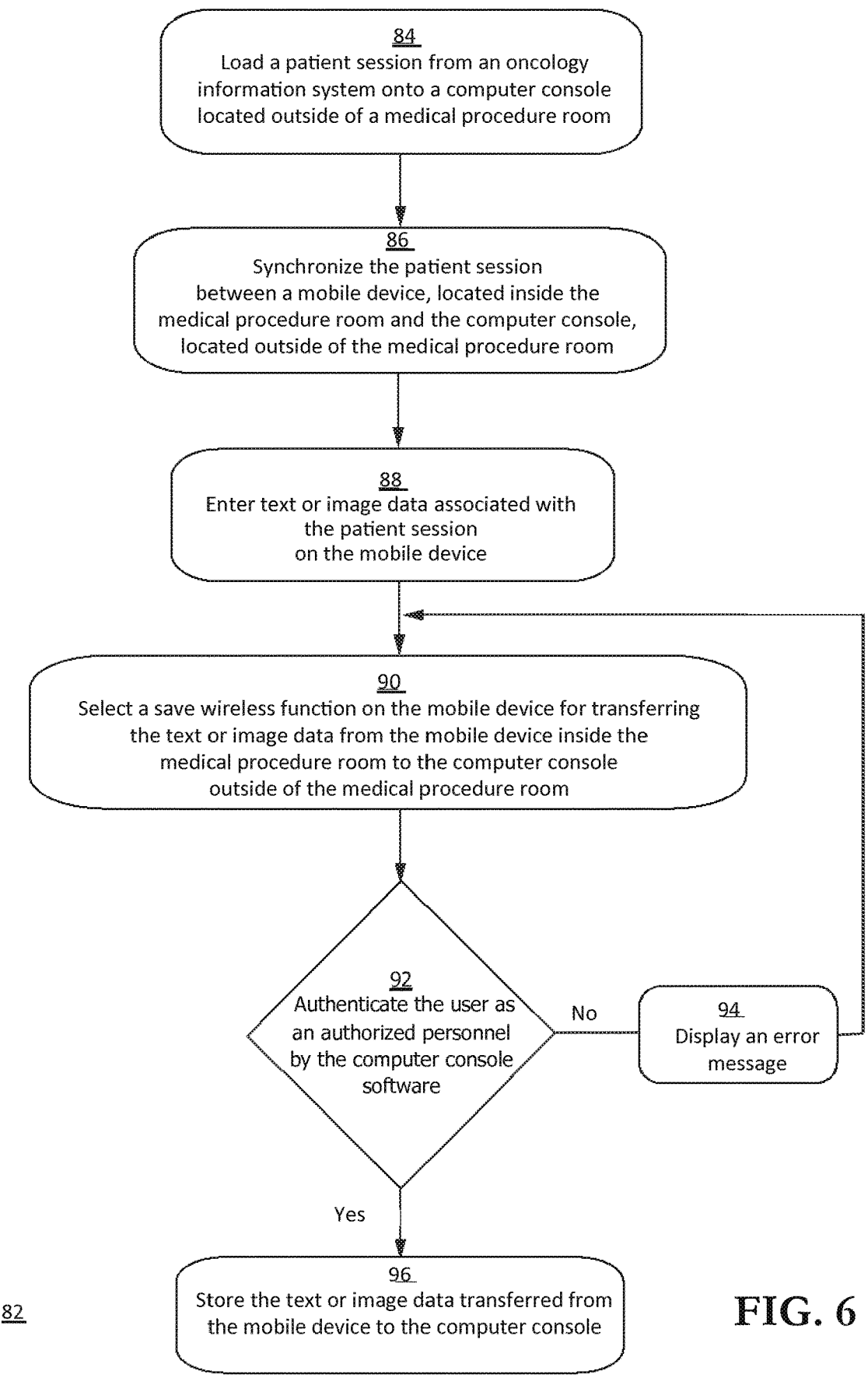
FIG. 6 is a flow chart illustrating the process of the mobile treatment engine for operation in a wireless networked treatment environment in accordance with the present invention.

FIG. 6 is a flow chart illustrating the process 82 of the mobile treatment engine 12a for operation in a wireless networked treatment environment. At step 84, the mobile treatment engine 12 is configured to load a patient session from an oncology information system onto the computer console 24a located outside a medical procedure room. At step 86, the synchronization module 52 is configured to synchronize the patient session between the mobile device 26a, located inside the medical procedure room 14a, and the computer console 24a, located outside the medical procedure room 16a. In other embodiments, an NFC can be installed in the medical procedure room 14a to provide a wireless access point that synchronizes data with the medical device control console 24a located outside the medical procedure room 14a. At step 88, the TEAM setup photo/notes component 54 is configured to capture the entry of text or image data associated with the patient session on the mobile device 26a. The mobile treatment engine 12a is configured to select a save wireless function on the mobile device for transferring the text or image data including the correct patient, plan and/field context from the mobile device 26a inside the medical procedure room 14a to the medical device control console 24a outside the medical procedure room 16. At step 92, the mobile treatment engine 12a is configured to authenticate the user as an authorized personnel by the computer console software. If the treater is not authenticated, the mobile treatment engine 12a is configured to display an error message at step 94, and the process returns to step 90. If the treater is properly authenticated, the mobile treatment engine 12a is configured to store the text or image data transferred from the mobile device 26a to the patient session active on the computer console 24a.

Figure 7:
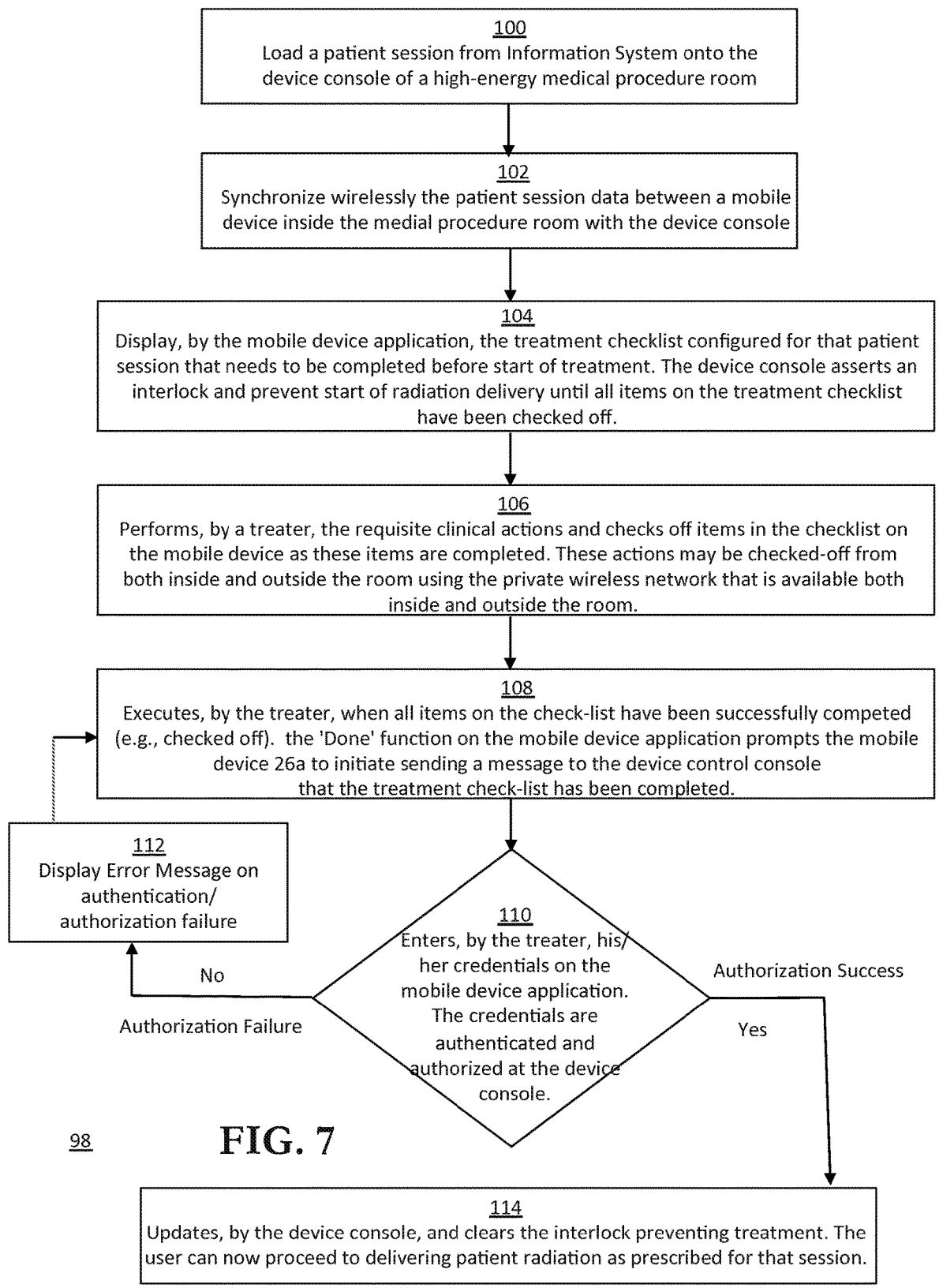
FIG. 7 is a flow chart illustrating the process of the TEAM for executing a treatment checklist for operation in a wireless networked treatment environment in accordance with the present invention.

FIG. 7 is a flow chart illustrating the process 98 of the mobile treatment engine for executing a treatment checklist for operation in a wireless networked treatment environment. At step 100, the mobile treatment engine 12a is configured to load a patient session from Information System onto the device console of the high-energy medical procedure room 14a. At step 102, the synchronization module 52 is configured to synchronize wirelessly the patient session data between the mobile device 26a inside the medical procedure room 14a with the medical device control console 24a. At step 104, the mobile treatment engine 12a is configured to display the treatment checklist configured for that patient session that needs to be completed before the start of treatment. The medical device control console 24a asserts an interlock and prevents start of radiation delivery until all items on the treatment checklist have been checked off. At step 106, the mobile treatment engine 12a is configured to perform by a treater (or a user) the requisite clinical actions and checks off items in the checklist on the mobile device 26a as the items are completed. These actions may be checked off from both inside the medical procedure 14a or outside the medical procedure room 14a using the private wireless network that is available both inside and outside the room. The mobile treatment engine 12a, at step 108, is configured to execute by the user when all items on the checklist have been successfully competed (i.e., checked-off). The 'Done' function on the mobile device application prompts the mobile device 26a to initiate by sending a message to the medical device control console 24a to indicate that the treatment checklist has been completed. At step 110, the mobile treatment engine 12a is configured to enter, by the treater, his/her credentials on the mobile device application. The credentials are authenticated and authorized at the device console. If the treater is not authenticated (i.e., authentication failure), at step 112, the mobile treatment engine 12a is configured to display an error message, and the process returns to step 108. If the user is properly authenticated (i.e., authentication success), the mobile treatment engine 12a is configured to update the medical device control console 24a, and clears the interlock preventing treatment. The user can now proceed to delivering patient radiation as prescribed for that session. One example of authentication on a touch screen display of the mobile device 26a is biometric authentication, as implemented in iPhone 5S.

Figure 8:
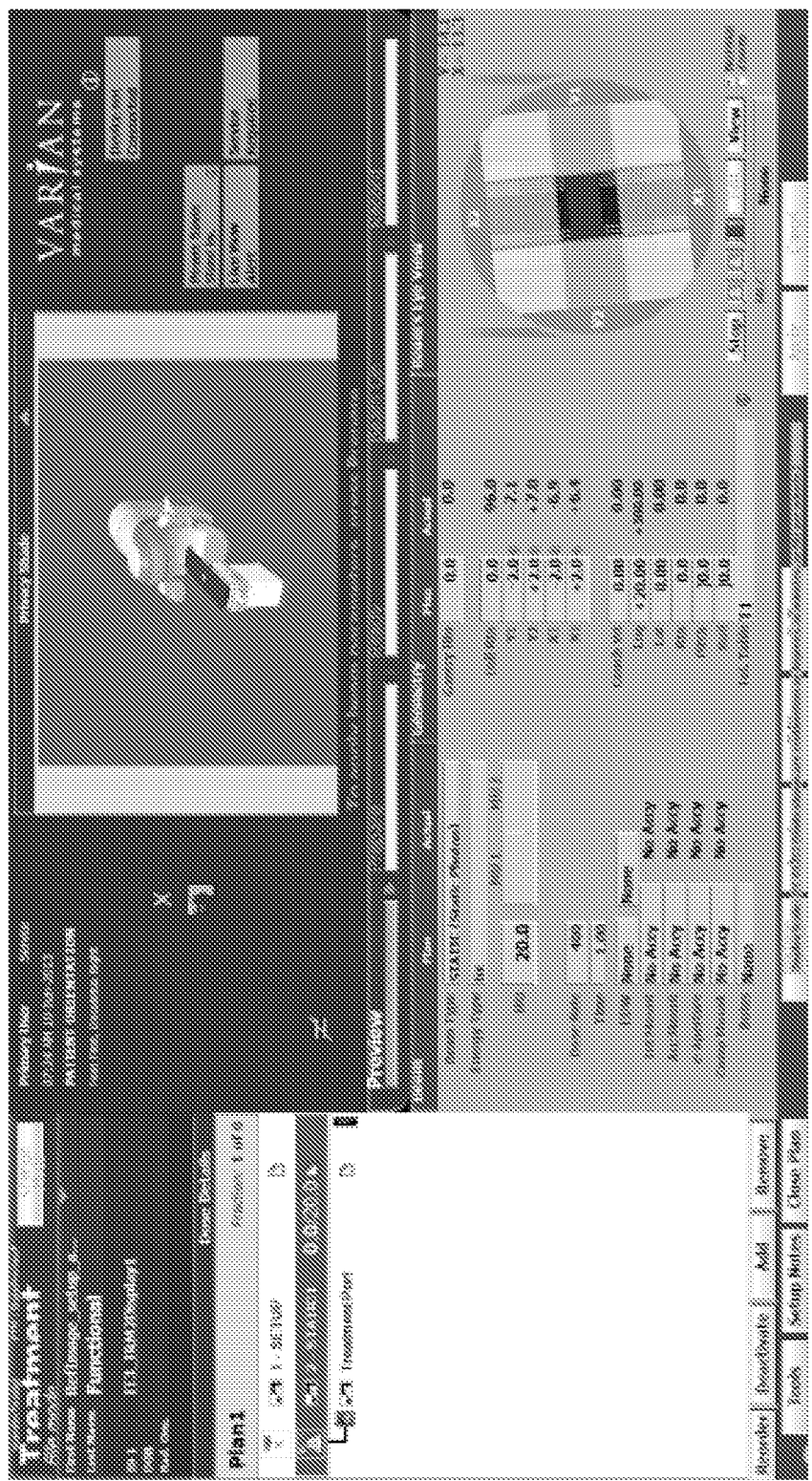
FIG. 8 is a sample screen shot illustrating a patient session that is loaded in a radiotherapy system, TrueBeam™, by Varian Medical Systems, in accordance with the present invention.
Figure 9:
FIG. 9 is a sample screen shot illustrating a patient treatment menu (also referred to as VTab) synchronized with one or more connected medical devices in accordance with the present invention.
Figure 10:
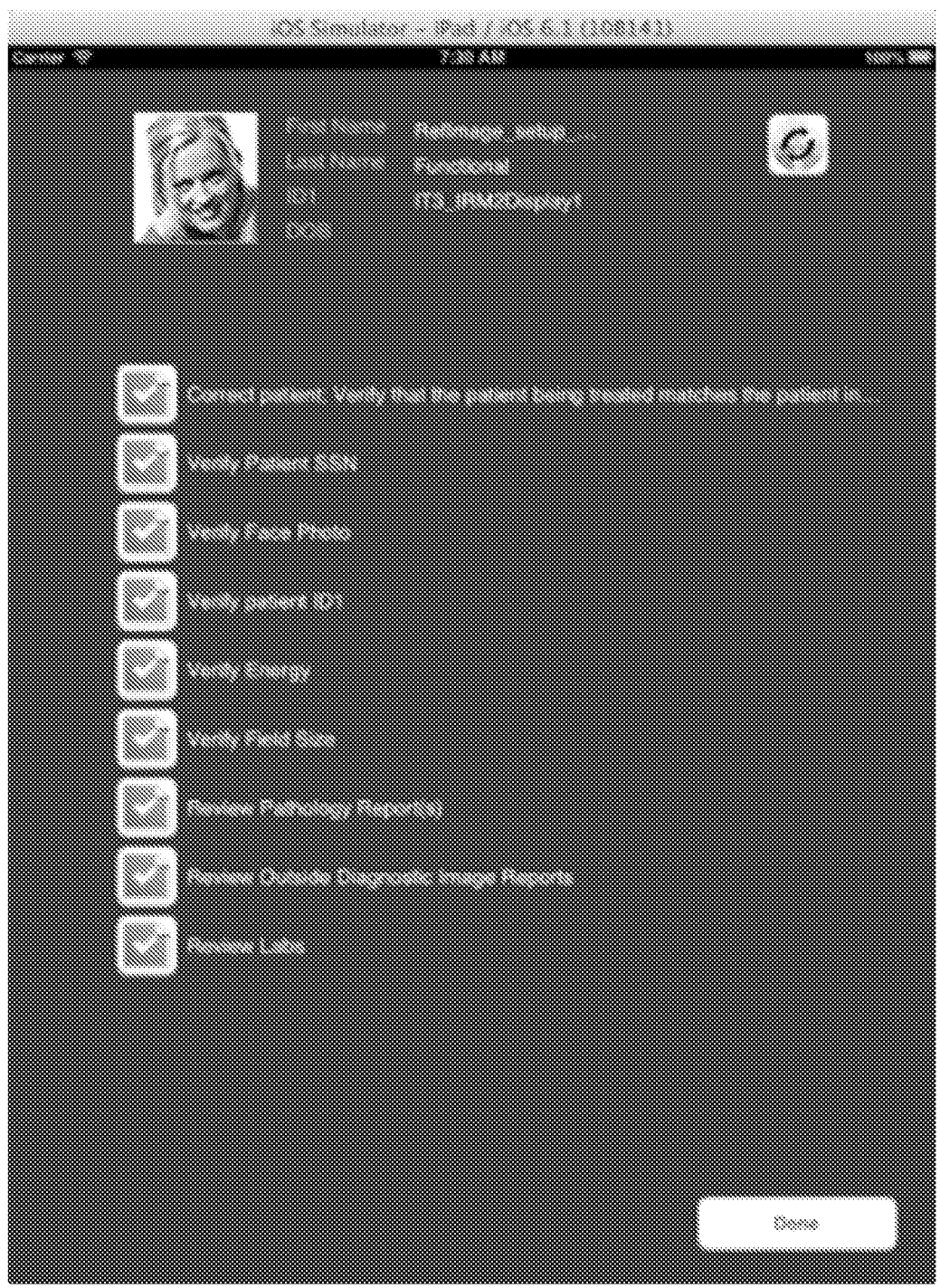
FIG. 10 is a sample screen shot illustrating a patient treatment menu, in which the patient treatment checklist has been completed in accordance with the present invention.
Figure 11:
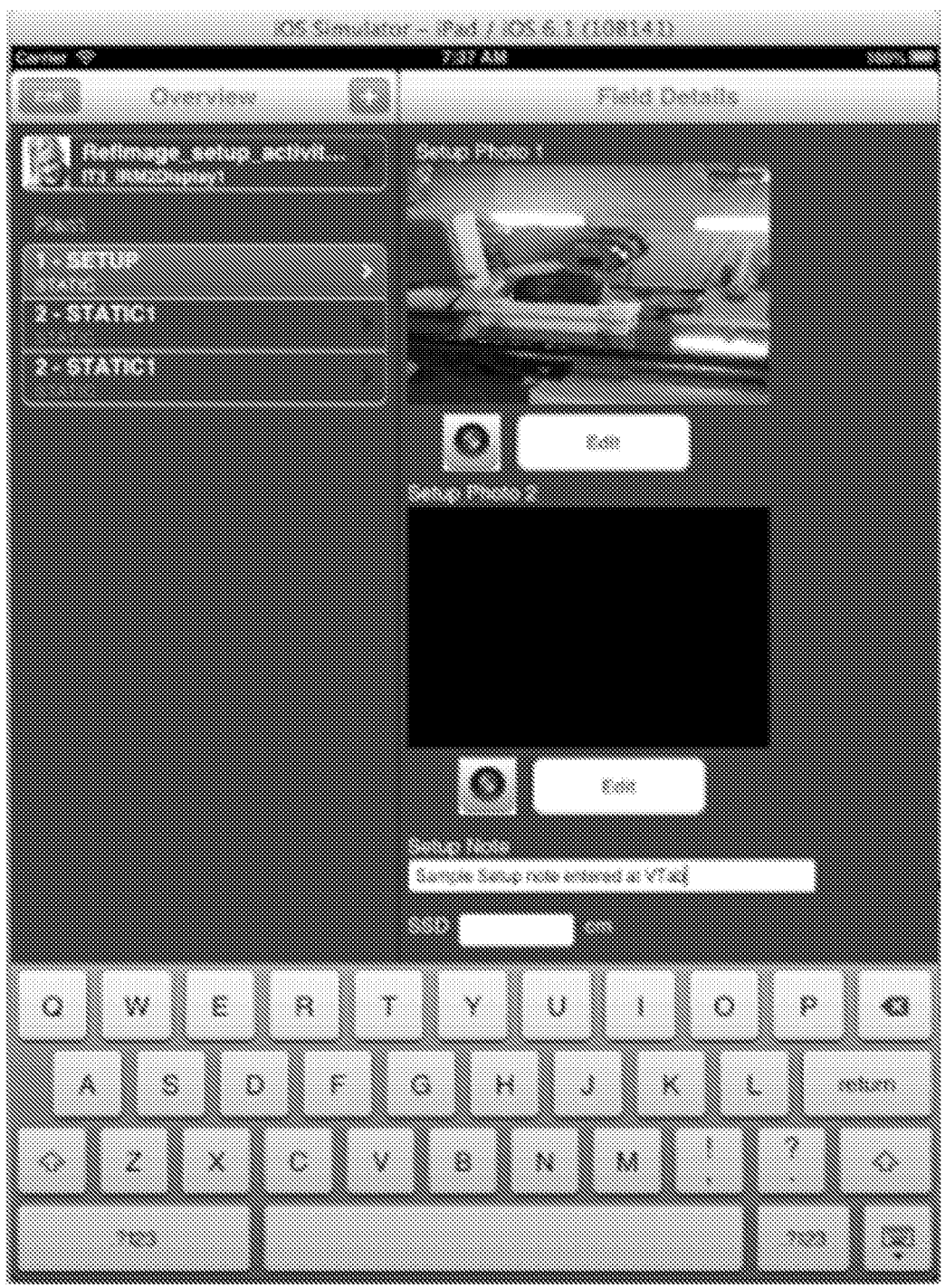
FIG. 11 is a sample screen shot illustrating a patient treatment menu for setting up photo and entering notes in accordance with the present invention.
Figure 12:
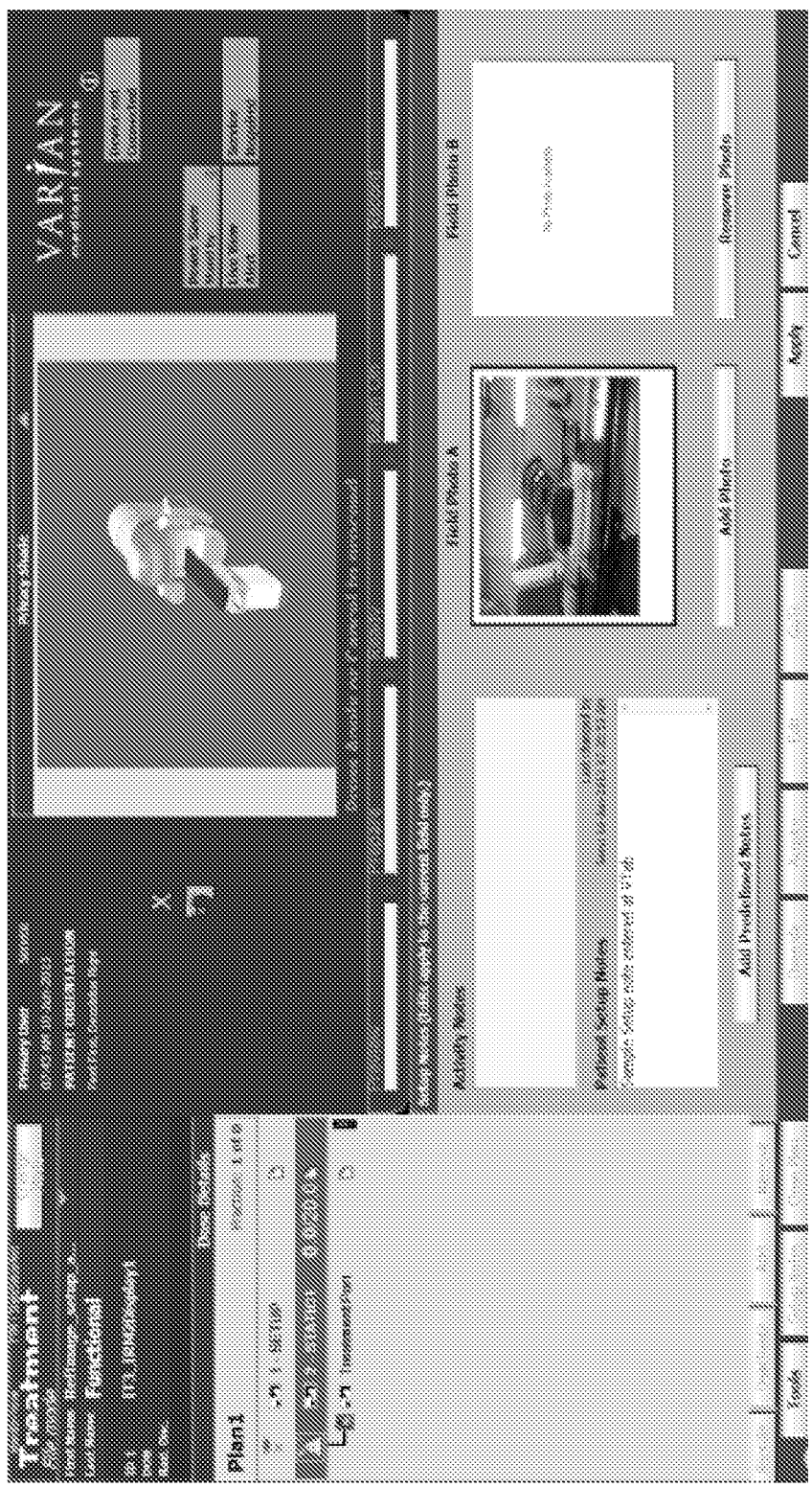
FIG. 12 is a sample screen shot illustrating a patient treatment menu for setting up photos and entering notes that are synchronized with TrueBeam™ console application in accordance with the present invention.

FIGS. 8 to 12 illustrate various screen shots. A sample screen shot in FIG. 8 illustrates a patient session that is loaded in a radiotherapy system, TrueBeam™, by Varian Medical Systems. FIG. 9 is a sample screen shot illustrating a patient treatment menu synchronized with one or more connected medical devices. In FIG. 10, there is a sample screen shot illustrating a patient treatment menu, in which the patient treatment checklist has been completed. FIG. 11 is a sample screen shot illustrating a patient treatment menu for setting up photos and entering notes in accordance with the present invention. A sample screen shot in FIG. 12 illustrates a patient treatment menu for setting up photos and entering notes that are synchronized with TrueBeam™ console application.

Figure 13:
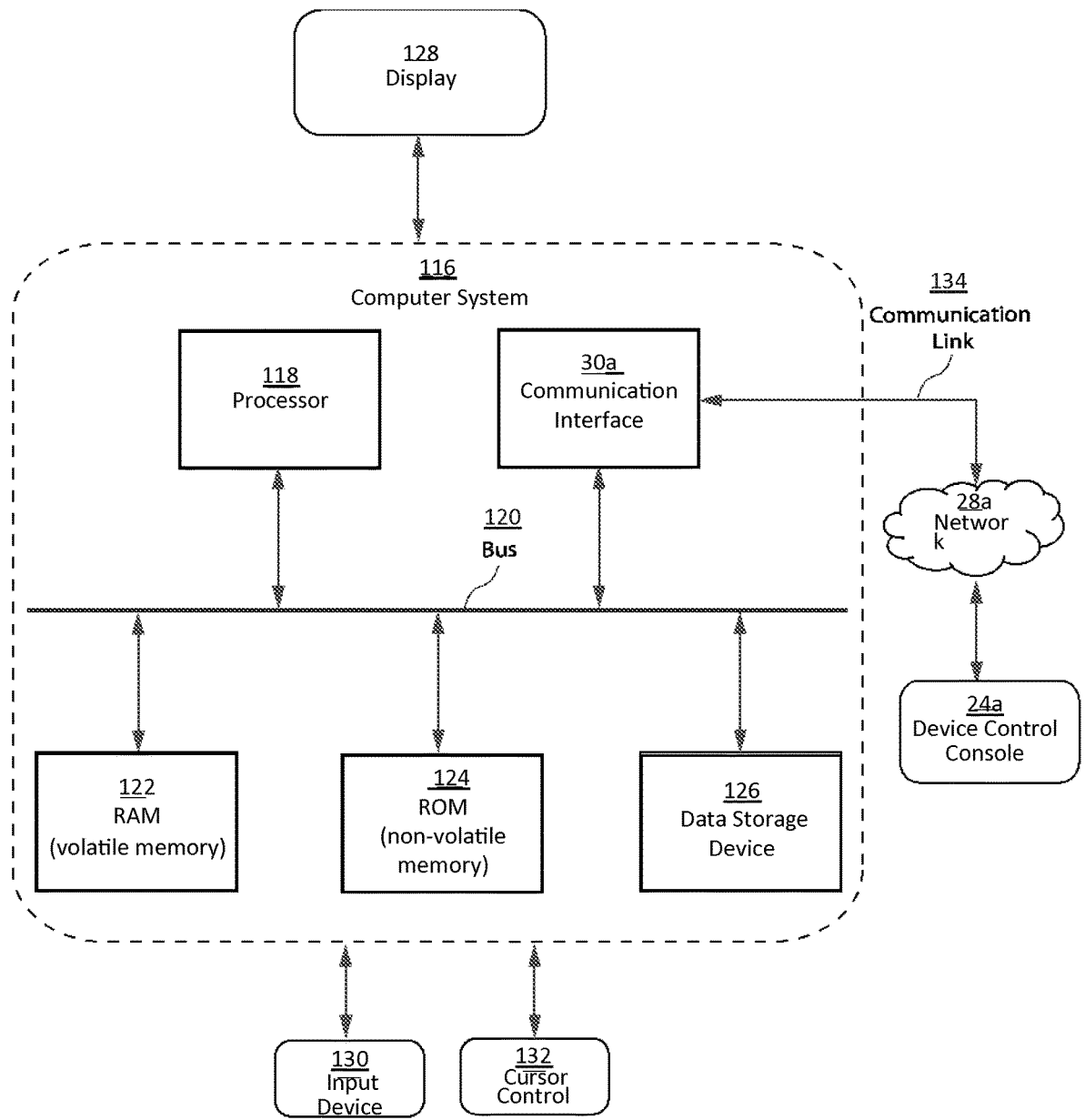
FIG. 13 is a block diagram illustrating an example of a computer device (including a tablet, a smartphone, a notebook computer, wearable devices such as a watch, glasses, etc.) on which computer-executable instructions to perform the methodologies discussed herein may be installed and run.

FIG. 13 is a block diagram illustrating an example of a computer device (including a tablet, a smartphone, a notebook computer, wearable devices such as a watch, glasses, etc.) on which computer-executable instructions to perform the methodologies discussed herein may be installed and run. A computer system 26a includes a processor 118 for processing information, and the processor 118 is coupled to a bus 120 or other communication medium for sending and receiving information. The processor 118 may be an example of the processor 118 of FIG. 13, or another processor that is used to perform various functions described herein. In some cases, the computer system 26a may be used to implement the processor 118 as a system-on-a-chip integrated circuit. The computer system 26a also includes a main memory 122, such as a random access memory (RAM) or other dynamic storage device, coupled to the bus 120 for storing information and instructions to be executed by the processor 18. The main memory 122 also may be used for storing temporary variables or other intermediate information during execution of instructions by the processor 118. The computer system 26a further includes a read only memory (ROM) 124 or other static storage device coupled to the bus 120 for storing static information and instructions for the processor 118. A data storage device 126, such as a magnetic disk (e.g., a hard disk drive), an optical disk, or a flash memory, is provided and coupled to the bus 120 for storing information and instructions. The computer system 26a (e.g., smartphone mobile devices, tablets, wearable computers, desktops, laptops) may operate on any operating system platform using Windows® by Microsoft Corporation, MacOS or iOS by Apple, Inc., Linux, UNIX, and/or ChromeOS/Android by Google Inc.

The computer system 26a may be coupled via the bus 120 to a display 128, such as a flat panel for displaying information to a user. An input device 130, including alphanumeric, pen or finger touchscreen input, and other keys, is coupled to the bus 120 for communicating information and command selections to the processor 118. Another type of user input device is cursor control 132, such as a mouse (either wired or wireless), a trackball, a laser remote mouse control, or cursor direction keys for communicating directional information and command selections to the processor 118 and for controlling cursor movement on the display 128. This input device typically has two degrees of freedom in two axes, a first axis (e.g., x) and a second axis (e.g., y), that allow the device to specify positions in a plane.

The computer system 26a may be used for performing various functions (e.g., calculation) in accordance with the embodiments described herein. According to one embodiment, such use is provided by the computer system 26a in response to the processor 118 executing one or more sequences of one or more instructions contained in the main memory 122. Such instructions may be read into the main memory 122 from another computer-readable medium, such as storage device 126. Execution of the sequences of instructions contained in the main memory 122 causes the processor 118 to perform the process steps described herein. One or more processors in a multi-processing arrangement may also be employed to execute the sequences of instructions contained in the main memory 122. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 118 for execution. Common forms of computer-readable media include, but are not limited to, non-volatile media, volatile media, transmission media, a floppy disk, a flexible disk, a hard disk, magnetic tape, any other magnetic medium, a CD-ROM, a DVD, a Blu-ray Disc, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read. Non-volatile media includes, for example, optical or magnetic disks, such as the storage device 126. Volatile media includes dynamic memory, such as the main memory 122. Transmission media includes coaxial cables, copper wire, and fiber optics. Transmission media can also take the form of acoustic or light waves, such as those generated during radio wave and infrared data communications.

Various forms of computer-readable media may be involved in carrying one or more sequences of one or more instructions to the processor 118 for execution. For example, the instructions may initially be carried on a magnetic disk of a remote computer. The remote computer can load the instructions into its dynamic memory and send the instructions over a communication link 134. The computer system 26a includes a communication interface 30a for receiving the data on the communication link 134. The bus 120 carries the data to the main memory 122, from which the processor 118 retrieves and executes the instructions. The instructions received by the main memory 122 may optionally be stored on the storage device 126 either before or after execution by the processor 118.

The communication interface 30a, which is coupled to the bus 120, provides a two-way data communication coupling to the network link 134 that is connected to a communication network 28a. For example, the communication interface 28a may be implemented in a variety of ways, such as an integrated services digital network (ISDN), a local area network (LAN) card to provide a data communication connection to a compatible LAN, a Wireless Local Area Network (WLAN) and Wide Area Network (WAN), Bluetooth, and a cellular data network (e.g. 3G, 4G). In wireless links, the communication interface 28a sends and receives electrical, electromagnetic or optical signals that carry data streams representing various types of information.

Alternatively, image files can be transported manually through a portable storage device like a USB flash drive for loading into the storage device 126 or main memory 122 of the computer system 116, without necessarily transmitting the image files to the communication interface 30a via the network 28a and the communication link 134.

The web browser is a software application for retrieving, presenting, and traversing a Uniform Resource Identifier (URI) on the World Wide Web provided by the cloud computer or web servers. One common type of URI begins with Hypertext Transfer Protocol (HTTP) and identifies a resource to be retrieved over the HTTP. A web browser may include, but is not limited to, browsers running on personal computer operating systems and browsers running on mobile phone platforms. The first type of web browsers may include Microsoft's Internet Explorer, Apple's Safari, Google's Chrome, and Mozilla's Firefox. The second type of web browsers may include the iPhone OS, Google Android, Nokia S60 and Palm WebOS. Examples of a URI include a web page, an image, a video, or other type of content.

The network 28a can be implemented as a wireless network, a wired network protocol or any suitable communication protocols, such as 3G (3rd generation mobile telecommunications), 4G (fourth-generation of cellular wireless standards), long term evolution (LTE), 5G, a wide area network (WAN), Wi-Fi™ like wireless local area network (WLAN) 802.11n, or a local area network (LAN) connection (internetwork—connected to either WAN or LAN), Ethernet, Bluebooth™, high frequency systems (e.g., 900 MHz, 2.4 GHz, and 5.6 GHz communication systems), infrared, transmission control protocol/internet protocol ("TCP/IP") (e.g., any of the protocols used in each of the TCP/IP layers), hypertext transfer protocol ("HTTP"), BitTorrent™, file transfer protocol ("FTP"), real-time transport protocol ("RTP"), real-time streaming protocol ("RTSP"), secure shell protocol ("SSH"), any other communications protocol, and other types of networks like a satellite, a cable network, or an optical network set-top boxes (STBs).

A SmartAuto includes an auto vehicle with a processor, a memory, a screen, with connection capabilities of Wireless Local Area Network (WLAN) and Wide Area Network (WAN), or an auto vehicle with a telecommunication slot connectable to a mobile device like iPods, iPhones, and iPads.

A SmartTV includes a television system having a telecommunication medium for transmitting and receiving moving video images (either monochromatic or color), still images and sound. The television system operates as a television, a computer, an entertainment center, and a storage device. The telecommunication medium of the television system includes a television set, television programming, television transmission, cable programming, cable transmission, satellite programming, satellite transmission, Internet programming, and Internet transmission.

Alternatively, the mobile device may be communicatively coupled to a cloud computer which is a browser-based operating system communicating through an Internet-based computing network that involves the provision of dynamically scalable and often virtualized resources as a service over the Internet, such as iCloud® available from Apple Inc. of Cupertino, Calif., Amazon Web Services (IaaS) and Elastic Compute Cloud (EC2) available from Amazon.com, Inc. of Seattle, Wash., SaaS and PaaS available from Google Inc. of Mountain View, Calif., Microsoft Azure Service Platform (Paas) available from Microsoft Corporation of Redmond, Wash., Sun Open Cloud Platform available from Oracle Corporation of Redwood City, Calif., and other cloud computing service providers.

Some portions of the above description describe the embodiments in terms of algorithmic descriptions and processes, e.g. as with the description within FIGS. 1-13. These operations (e.g., the processes described above), while described functionally, computationally, or logically, are understood to be implemented by computer programs or equivalent electrical circuits, microcode, or the like. The computer programs are typically embedded as instructions that can be stored on a tangible computer readable storage medium (e.g., flash drive disk, or memory) and are executable by a processor, for example, as described in FIGS. 1-13. Furthermore, it has also proven convenient at times to refer to these arrangements of operations as modules, without loss of generality. The operations described and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still cooperate or interact with each other. The embodiments are not limited in this context.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to "an inclusive or" and "not to an exclusive or". For example, a condition A or B is satisfied by any one of the following: A is true (or present) and B is false (or not present), A is false (or not present) and B is true (or present), and both A and B are true (or present).

The terms "a" or "an," as used herein, are defined as one or more than one. The term "plurality," as used herein, is defined as two or more than two. The term "another," as used herein, is defined as at least a second or more.

The invention can be implemented in numerous ways, including as a process, an apparatus, and a system. In this specification, these implementations, or any other form that the invention may take, may be referred to as techniques. In general, the order of the connections of disclosed apparatus may be altered within the scope of the invention.

The present invention has been described in particular detail with respect to one possible embodiment. Those skilled in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. In addition, the particular division of functionality between the various system components described herein is merely exemplary, and not mandatory; functions performed by a single system component may instead be performed by multiple components, and functions performed by multiple components may instead be performed by a single component.

An ordinary artisan should require no additional explanation in developing the methods and systems described herein but may find some possibly helpful guidance in the preparation of these methods and systems by examining standard reference works in the relevant art.

These and other changes can be made to the invention in light of the above detailed description. In general, in the following claims, the terms used should not be construed to limit the invention to the specific embodiments disclosed in the specification and the claims, but should be construed to include all methods and systems that operate under the claims set forth herein below. Accordingly, the invention is not limited by the disclosure, but instead its scope is to be determined entirely by the following claims.

What is claimed is:

1. A method for communication between a mobile device associated with a medical imaging machine positioned inside a room and a console outside the room using a first networking device positioned outside the room and a second networking device positioned inside the room, the room comprising a maze positioned between the mobile device and the second networking device, the maze shielding the second networking device from radiation emitted from the medical imaging machine, the method comprising:

loading, by the console, a patient session, wherein the console is programmed to control the medical imaging machine;

mapping, by the console, a unique identifier associated with the mobile device to the medical imaging machine;

performing, by the console, a wireless synchronization of the patient session between the console and the mobile device, wherein the wireless synchronization is over the first networking device and the second networking device, wherein the mobile device includes a display;

causing, by the console, a user interface to be presented on the display over the first networking device and the second networking device, wherein the user interface is programmed to receive a plurality of end user inputs related to the patient session;

asserting, by the console, an interlock to the medical imaging machine, based on the mapping, such that the medical imaging machine is prevented from imaging for the patient session until the end user inputs have been entered onto the display of the mobile device mapped to the medical imaging machine;

receiving, by the console, a message from the mobile device over the first networking device and the second networking device, wherein the message is indicative of the end user inputs being entered, wherein the patient session relates to the message;

authenticating, by the console, a credential received from the mobile device over the first networking device and the second networking device after the message, wherein the patient session relates to the credential; and authorizing, by the console, the interlock to be cleared based on the credential being authenticated such that the medical imaging machine is able to image for the patient session.

2. The method of claim 1, wherein the console is programmed to communicate with the medical imaging machine over a wide area network.

3. The method of claim 1, wherein the console is programmed to communicate with the medical imaging machine over a satellite network.

4. The method of claim 1, wherein the medical imaging machine is a first medical imaging machine, wherein the console is in communication with a plurality of medical imaging machines, wherein the medical imaging machines include the medical imaging machine.

5. The method of claim 4, wherein the console is programmed to communicate with at least one of the medical imaging machines over at least one of a wide area network or a satellite network.

6. The method of claim 4, wherein the console is in a one-to-many relationship with the medical imaging machines.

7. The method of claim 1, wherein the user interface includes a checklist including a plurality of end user input elements programmed to receive the end user inputs, wherein the end user inputs are entered via the end user input elements.

8. The method of claim 1, wherein at least one of the end user inputs includes at least one of a text or an image.

9. The method of claim 1, wherein the display is a first display, wherein the console includes a second display, wherein the user interface is a first user interface, wherein the console is programmed to present a second user interface on the second display while the first display presents the first user interface, wherein the end user inputs is a plurality of first end user inputs, wherein the second user interface is programmed to receive a plurality of second end user inputs related to the patient session, wherein the first end user inputs and the second end user inputs correspond to each other, wherein the message is indicative of the end user inputs being entered via the first end user inputs and the second end user inputs.

10. The method of claim 1, wherein the room includes a door, wherein the maze shields the second networking device from the medical imaging machine when the door is closed and the medical imagining machine is imaging for the patient session, wherein at least one of the user inputs is being entered for the patient session before the message is received while the door is open and the medical imaging machine is not imaging for the patient session.

11. A system for communicating between a mobile device associated with a medical imaging machine positioned inside a room and a console outside the room using a first networking device positioned outside the room and a second networking device positioned inside the room, the room comprising a maze positioned between the mobile device and the second networking device, the maze shielding the second networking device from radiation emitted from the medical imaging machine, the system comprising:
the console programmed to:
load a patient session, wherein the console is programmed to control the medical imaging machine;
perform a wireless synchronization of the patient session between the console and the mobile device positioned inside the room, wherein the wireless synchronization is over the first networking device and the second networking device, wherein the mobile device includes a display;
map a unique identifier associated with the mobile device to the medical imaging machine;
cause a user interface to be presented on the display over the first networking device and the second networking device, wherein the user interface is programmed to receive a plurality of end user inputs related to the patient session;
assert an interlock to the medical imaging machine, based on the mapping, such that the medical imaging machine is prevented from imaging for the patient session until the end user inputs have been entered onto the display of the mobile device mapped to the medical imaging machine;
receive a message from the mobile device over the first networking device and the second networking device, wherein the message is indicative of the end user inputs being entered, wherein the patient session relates to the message;
authenticate a credential received from the mobile device over the first networking device and the second networking device after the message, wherein the patient session relates to the credential; and
authorize the interlock to be cleared based on the credential being authenticated such that the medical imaging machine is able to image for the patient session.

12. The system of claim 11, wherein the console is programmed to communicate with the medical imaging machine over a wide area network.

13. The system of claim 11, wherein the console is programmed to communicate with the medical imaging machine over a satellite network.

14. The system of claim 11, wherein the medical imaging machine is a first medical imaging machine, wherein the console is in communication with a plurality of medical imaging machines, wherein the medical imaging machines include the medical imaging machine.

15. The system of claim 14, wherein the console is programmed to communicate with at least one of the medical imaging machines over at least one of a wide area network or a satellite network.

16. The system of claim 14, wherein the console is in a one-to-many relationship with the medical imaging machines.

17. The system of claim 11, wherein the user interface includes a checklist including a plurality of end user input elements programmed to receive the end user inputs, wherein the end user inputs are entered via the end user input elements.

18. The system of claim 11, wherein at least one of the end user inputs includes at least one of a text or an image.

19. The system of claim 11, wherein the display is a first display, wherein the console includes a second display, wherein the user interface is a first user interface, wherein the console is programmed to present a second user interface on the second display while the first display presents the first user interface, wherein the end user inputs is a plurality of first end user inputs, wherein the second user interface is programmed to receive a plurality of second end user inputs related to the patient session, wherein the first end user inputs and the second end user inputs correspond to each other, wherein the message is indicative of the end user inputs being entered via the first end user inputs and the second end user inputs.

20. The system of claim 11, wherein the room includes a door, wherein the maze shields the second networking device from the medical imaging machine when the door is closed and the medical imagining machine is imaging for the patient session, wherein at least one of the user inputs is being entered for the patient session before the message is received while the door is open and the medical imaging machine is not imaging for the patient session.

* * * * *